United States Patent
Schmitt et al.

(10) Patent No.: US 9,738,547 B2
(45) Date of Patent: Aug. 22, 2017

(54) ULTRAVIOLET LIGHT SANITIZING ASSEMBLY WITH FLOW SWITCH AND KEYED LAMP

(71) Applicant: Watts Regulator Co., North Andover, MA (US)

(72) Inventors: Craig A. Schmitt, Phoenix, AZ (US); Michael Sarchese, Guelph (CA)

(73) Assignee: WATTS REGULATOR CO., North Andover, MA (US)

( * ) Notice: Subject to any disclaimer, the term of this patent is extended or adjusted under 35 U.S.C. 154(b) by 0 days.

(21) Appl. No.: 15/132,686

(22) Filed: Apr. 19, 2016

(65) Prior Publication Data

US 2016/0326021 A1    Nov. 10, 2016

Related U.S. Application Data

(60) Provisional application No. 62/150,827, filed on Apr. 21, 2015.

(51) Int. Cl.
*A61L 2/10* (2006.01)
*C02F 1/32* (2006.01)
*A61L 2/24* (2006.01)

(52) U.S. Cl.
CPC ............... *C02F 1/325* (2013.01); *A61L 2/10* (2013.01); *A61L 2/24* (2013.01); *A61L 2202/11* (2013.01); *A61L 2202/14* (2013.01); *C02F 2201/326* (2013.01)

(58) Field of Classification Search
USPC ... 250/432 R, 428, 433, 434, 435, 436, 437, 250/438, 453.11, 454.11, 455.11, 492.1, 250/504 R; 422/22, 24
See application file for complete search history.

(56) References Cited

U.S. PATENT DOCUMENTS

| | | |
|---|---|---|
| D140,141 S | 1/1945 | Glatthar et al. |
| 3,683,177 A | 8/1972 | Veloz |
| 4,017,734 A | 4/1977 | Ross |
| 4,700,101 A | 10/1987 | Ellner et al. |
| (Continued) | | |

FOREIGN PATENT DOCUMENTS

WO    WO-0068152 A1    11/2000

OTHER PUBLICATIONS

European Search Report for EP Application No. 16275056.6 dated Jan. 20, 2017, 6 pages.

*Primary Examiner* — Nicole Ippolito
(74) *Attorney, Agent, or Firm* — Burns & Levinson LLP; George N. Chaclas

(57) ABSTRACT

An ultra-violet (UV) assembly for treating a fluid with UV light has a housing. A mounting bracket defines a slot and a hollow. A UV source includes: a tab that twist-locks in the slot; a connector that aligns with the hollow; and an RFID tag. An RFID antenna interacts with the RFID tag to emit a RFID tag position signal. A flow switch sends a flow signal. The flow switch includes: a guide; a shaft slidably mounted to the guide; a disc on the shaft; a magnet coupled to the shaft; and a sensor for generating a magnet position signal. During no flow, a spring biases the shaft so that the magnet is positioned to be detected by the sensor. During flow, the flow applies pressure to move the disc and, in turn, the magnet moves to be positioned to not be detected by the sensor.

9 Claims, 9 Drawing Sheets

(56) References Cited

U.S. PATENT DOCUMENTS

| | | |
|---|---|---|
| 5,334,905 A | 8/1994 | Ullrich |
| 5,393,419 A | 2/1995 | Tiede et al. |
| 5,547,590 A | 8/1996 | Szabo |
| 6,472,624 B1 * | 10/2002 | Harris .................. H01H 35/405 |
| | | 200/81.9 M |
| 6,645,277 B1 * | 11/2003 | Franz ................... B01D 46/008 |
| | | 210/85 |
| 6,960,321 B1 | 11/2005 | Ludwig |
| D598,578 S | 8/2009 | Hanley |
| D598,579 S | 8/2009 | Hanley |
| 7,569,981 B1 | 8/2009 | Ciancanelli |
| 8,395,134 B2 | 3/2013 | Penhale et al. |
| 8,674,322 B2 | 3/2014 | Kohler |
| 8,890,087 B2 | 11/2014 | Ben-David et al. |
| 2009/0261264 A1 | 10/2009 | Hormann |
| 2012/0234166 A1 * | 9/2012 | Markham ................. A61L 9/20 |
| | | 95/214 |
| 2014/0077696 A1 | 3/2014 | Kuennen et al. |
| 2014/0158905 A1 | 6/2014 | Hoang |
| 2014/0352799 A1 * | 12/2014 | Rosko ...................... C02F 1/78 |
| | | 137/237 |

* cited by examiner

US 9,738,547 B2

ULTRAVIOLET LIGHT SANITIZING ASSEMBLY WITH FLOW SWITCH AND KEYED LAMP

CROSS REFERENCE TO RELATED APPLICATION

This non-provisional patent application is claims priority from and the benefit of U.S. Provisional Patent Application No. 62/150,827 filed Apr. 21, 2015, U.S. Design Pat. application No. 29/524,583 filed Apr. 21, 2015, and U.S. Non-Provisonal patent application Ser. No. 14/807,184 filed Jul. 23, 2015, which claims priority to and the benefit of U.S. Provisional Patent Application No. 62/027,993 filed Jul. 23, 2014, each of which is incorporated herein by reference in its entirety.

BACKGROUND OF THE DISCLOSURE

1. Field of the Disclosure

The subject disclosure relates to assemblies and methods for sanitizing water using ultraviolet light (hereafter abbreviated to "UV" or UV light") and, more particularly to safer and more efficient UV sanitizing assemblies and methods.

2. Background of the Related Art

Treatment of fluids via irradiation with ultraviolet light is known to be an effective method for disinfection without chemicals. The applications are as varied as water, food, swimming pools and the like in both industrial and residential applications. The typical approach is treatment of fluids within an enclosed treatment zone that is irradiated with ultraviolet light as shown in FIG. 1, which is a cross-sectional view of a UV treatment system. The objective of these systems, as for any type of photo-reactor, is to provide a uniform amount of UV energy to each individual element (e.g., contaminant molecule, microorganism) as the contaminant passes through the treatment zone.

Referring to FIG. 1, a typical prior-art UV treatment vessel 10 is shown. In the vessel 10, a UV treatment zone 11 is contained within a chamber 12 which is in fluid communication with an inlet port 13 and an outlet port 14. Fluid entering the chamber 12 is represented by the arrow "a" and fluid exiting the chamber 12 is represented by the arrow "b". At least one UV light emitting source assembly 15 is located within the chamber 12 to provide radiant UV energy within the UV treatment zone 11, the flow of which is indicated by the arrow "c". Many forms of UV emitting source assemblies are available, including those utilizing mercury vapor lamps or UV light emitting diodes.

The UV source 15 is housed within a UV transparent sleeve 16. The UV source 15 receives electrical energy via wires 17 from an electrical power supply not shown designed to suit the specific type of UV source 15. A sealing cap 18 with an o-ring seal 19 seals the outside of transparent sleeve 16 to the chamber 12, allowing a passageway for the UV source 15 and wires 17 while preventing undesirable escape of fluid.

SUMMARY OF THE INVENTION

There are problems associated with UV treatment assemblies. The present technology provides improvements to the current art, by providing enhanced safety features. For example, a keyed lamp assembly that prevents inadvertent operation is disclosed. Also, a very sensitive flow switch for UV assemblies is disclosed.

One embodiment of the subject technology is directed to an ultra-violet (UV) light source assembly for treating a fluid with UV light has a housing. A mounting bracket defines a slot and a hollow. A UV source includes: a tab that twist-locks in the slot; a connector that aligns with the hollow; and an RFID tag. An RFID antenna interacts with the RFID tag to emit a first signal indicating position of the UV source. A flow switch sends a second signal indicating fluid flow. The flow switch includes: a guide; a shaft slidably mounted to the guide; a disc on the shaft; a collar on the shaft; a spring mounted between the collar and the guide to bias the shaft toward a closed position; a magnet coupled to the shaft; and a sensor for generating the second signal based on proximity of the magnet thereto, wherein, during substantially no flow, the spring biases the plunger assembly so that the magnet is positioned to be detected by the sensor, and during flow, the flow applies pressure to move the disc and, in turn, the magnet moves to be positioned to not be detected by the sensor.

The UV light source assembly may also include a ballast controller for receiving and processing the first and second signals, wherein the ballast controller power the UV source based upon the first and second signals. The ballast controller can also receive a signal indicating a flow rate and adjusts an output of the UV source based upon the flow rate. The flow rate signal may come from the flow switch or another sensor. The ballast controller can record operational statistics of the UV source to determine when to replace the UV source. The operational statistics can be stored in the RFID tag to prevent unintended over-use among other things described herein.

Another embodiment of the subject technology is directed to an ultra-violet (UV) light source assembly for treating a fluid with UV light including a tubular housing defining: an interior chamber having a treatment zone; an inlet; and an outlet so that the fluid entering the inlet passes through the treatment zone. A mounting bracket couples to the tubular housing and defines at least one slot and a hollow. A UV source mounts in the interior chamber for supplying UV light to the treatment zone. The UV source includes: at least one tab that twist-locks in the slot; a connector that aligns with the hollow when locked for cabling to a ballast controller; and an RFID tag. An RFID antenna couples to the mounting bracket so that in when locked, the RFID antenna interacts with the RFID tag to emit a signal.

One embodiment of the subject technology is directed to a flow switch for an interior chamber of an ultra-violet light assembly. The interior chamber is defined by a housing having an inlet along an axis and a large diameter portion of the housing adjacent the inlet flares outward from the axis. The flow switch includes a guide fixed in the inlet. The guide has a ring shaped body with internal vanes defining a central aperture surrounded by at leat one flowpath. A plunger assembly has a disc and a shaft extending from the disc, wherein the shaft is coupled in the central aperture for sliding motion along the axis and the disc is sized and configured to move within the inlet. A collar couples to a distal end of the shaft for retaining the shaft within the central aperture. A spring mounts between the collar and the guide to bias the plunger assembly toward a closed position. A magnet couples to the plunger assembly for motion therewith and a magnet sensor mounts to the housing for determining proximity of the magnet. In the closed position during little or no flow through the inlet, the spring biases the plunger assembly so that the magnet is positioned to be detected by the sensor. In an open position during flow through the inlet, the flow applies pressure to the disc and, in turn, the disc moves into the large diameter portion of the housing and the magnet moves to be positioned to not be detected by the sensor.

It should be appreciated that the present technology can be implemented and utilized in numerous ways, including without limitation as a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those having ordinary skill in the art to which the disclosed technology appertains will more readily understand how to make and use the same, reference may be had to the following drawings.

DETAILED DESCRIPTION OF PREFERRED EMBODIMENTS

The present disclosure overcomes many of the problems associated with prior art UV assemblies. The advantages, and other features of the assemblies and methods disclosed herein, will become more readily apparent to those having ordinary skill in the art from the following detailed description of certain preferred embodiments taken in conjunction with the drawings which set forth representative embodiments of the present invention. All relative descriptions herein such as left, right, up, and down are with reference to the Figures, and not meant in a limiting sense.

UV System with Lamp Key Embodiments

Figure 1:
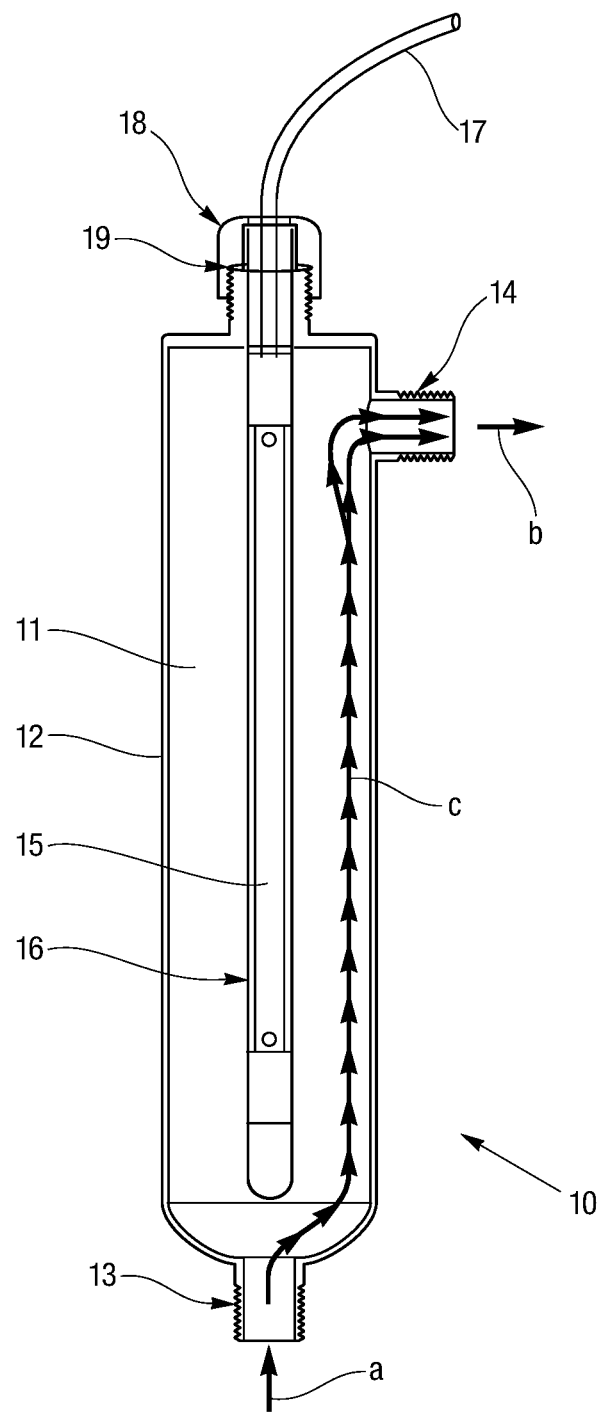
FIG. 1 is a cross-sectional view of a prior art UV assembly.
Figure 2A:
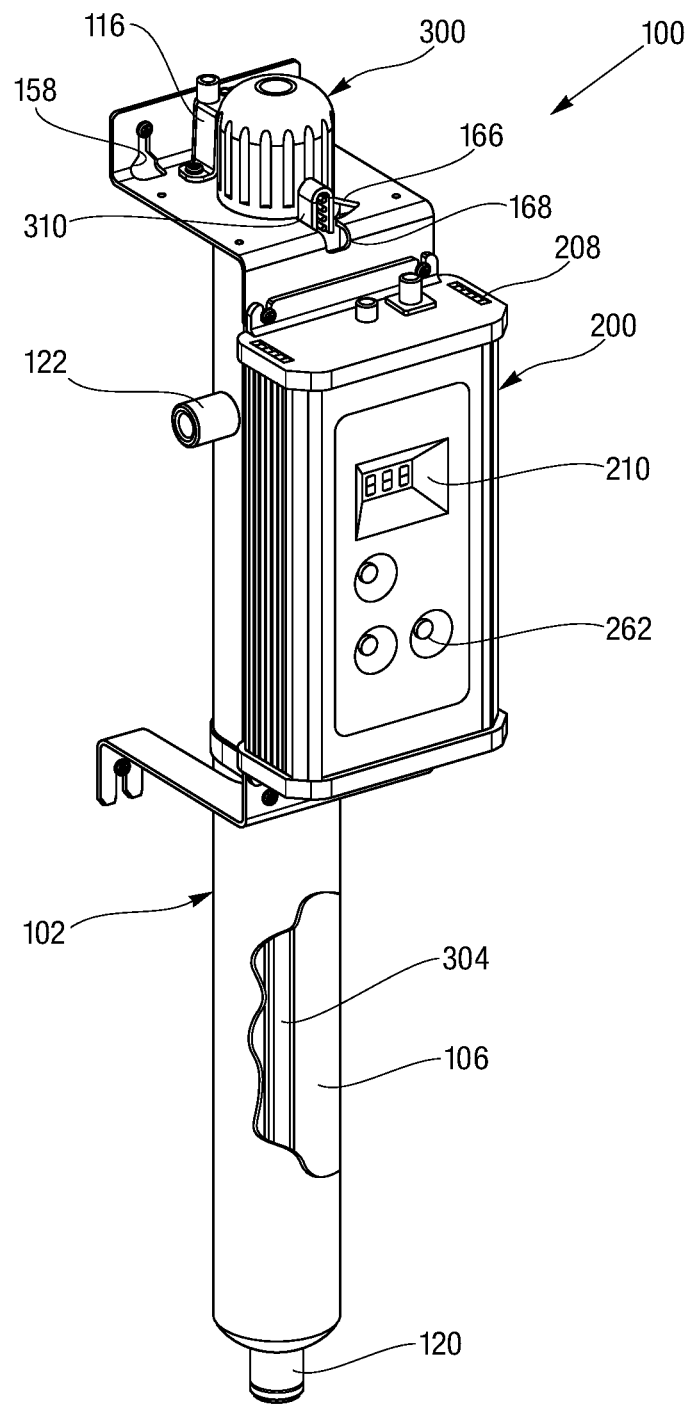
FIG. 2A is a perspective view of a UV assembly in accordance with the subject technology.
Figure 2B:
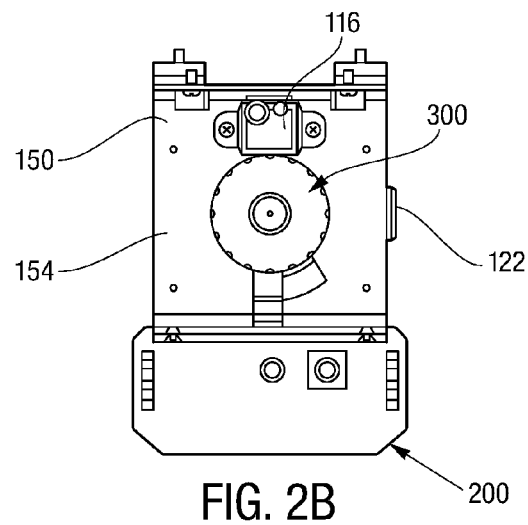
FIG. 2B is a top view of a UV assembly in accordance with the subject technology.
Figure 2C:
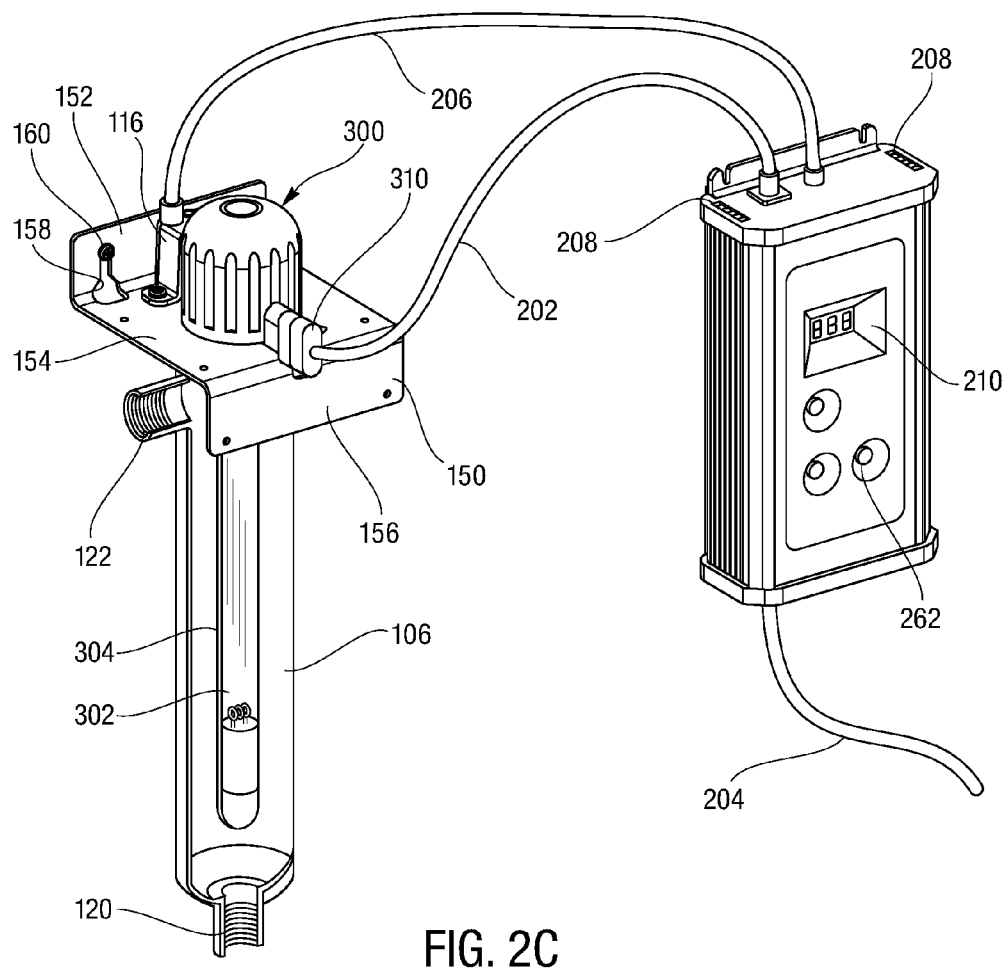
FIG. 2C is a perspective view of a UV assembly with the ballast controller separated in accordance with the subject technology.

Referring now to FIGS. 2A-2C, various perspective views and a top view of a UV assembly 100 are shown with a housing 102 in partial cut-away in accordance with the subject technology. In brief overview, the UV assembly 100 includes lamp key elements that prevent accidental exposure to UV light. The lamp key elements also provide increased reliability by eliminating the need to manually reset operational parameters related to the UV source when replacing said UV source, and to prevent use of improper UV sources. Further, these advantages and more are accomplished at a relatively low cost.

The UV assembly 100 includes a ballast controller 200 and UV source 300 coupled to the tubular housing 102. The ballast controller 200 is a power source and control center for the UV assembly 100. Preferably, the ballast controller 200 generates a constant current output to drive the UV source 300 at optimal efficiency and regulate dosage transmitted into the treated fluid. The ballast controller 200 controls the UV source 300 through a cable 202 connected to a bulb connector 310 (best seen in FIG. 3A). As such, the ballast controller 200 may be remotely mounted as best seen in FIG. 2C. Alternatively, the ballast controller 200 is mounted to a mounting bracket 150 as shown in FIGS. 2A and 2B. The ballast controller 200 also connects by a cable 204 to a power source (not shown) such as a 100V-240V/50-60 Hz supply.

The UV assembly 100 may includes sensors and devices that connect to the ballast controller 200. For example, an antenna housing 116 contains an antenna and other components that generate an electric field required to operate a RFID tag as described below. The antenna housing 116 is connected via the cable 206 to the ballast controller 200. The antenna housing 116 is fixed to the mounting bracket 150. The ballast controller 200 also includes additional output/input connectors 208 for expansion capabilities.

The ballast controller 200 has a graphic display 210 for providing information related to the UV assembly 100. Preferably, the graphic display 210 is 2.1 by 1.5 inches. The display 210 has a plurality of different screens. The graphic display 210 is typically a touch screen as is known in the art for allowing user interaction. Each screen may have areas that display various information as icons, graphics, numbs, letters, etc. as necessary to accomplish operation in accordance with the subject technology. In one embodiment, the display 210 includes a touch screen that can present a keypad and other interactive buttons.

Typically, the graphic display 210 would provide a boot screen during power up. During the power up, if the ballast controller 200 detects an error in the UV assembly 100 such as an invalid lamp, the graphic display 210 would provide an indication of the error with further instructions. The ballast controller 200 also includes buttons 262 for powering on/off, reset, interaction with the graphic display 210 and the like as needed for the operation described herewith.

By user selection, the graphic display 210 would also include a home screen that provides information such as lamp life, UV assembly status (e.g., warming up, sensor failure, over-temperature etc.). Additional screens indicate the total system operating time, dealer contact information, replacement lamp information, replacement sleeve information and the like. Each of screens is available from a setup screen via branching menus and the like.

The UV assembly 100 may be part of an overall system (not shown). The overall system may include scale prevention, water softening, chemical feed(s), reverse osmosis, media filtration and the like to create a complete fluid treatment system. Further, removing dissolved substances such as hardness minerals, iron, manganese, tannins as well as reducing the turbidity and color improves the disinfection performance of the UV assembly 100. The UV assembly 100 is also protected by such additional treatment. As pretreatment for reverse osmosis, the UV assembly 100 protects membranes from bio-films or downstream equipment from biological fouling.

Figure 2D:
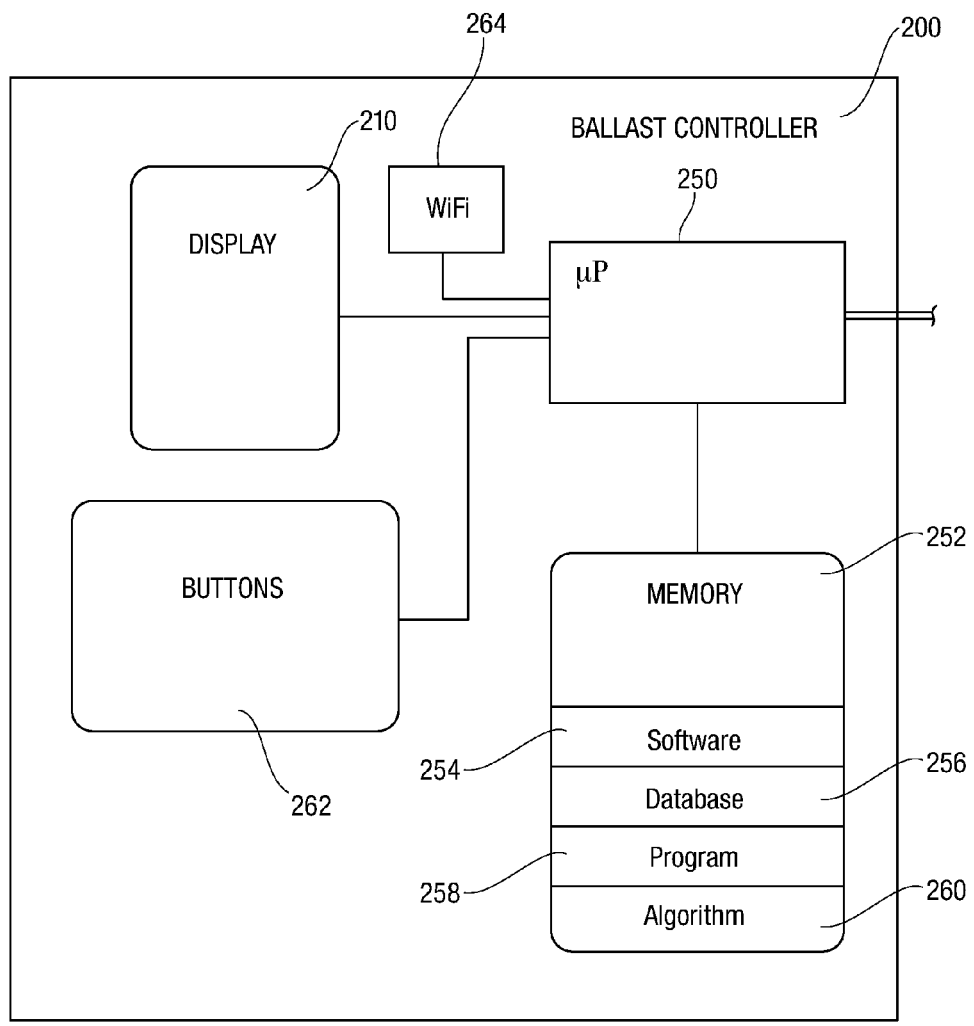
FIG. 2D is a somewhat schematic view of the ballast controller in accordance with the subject technology.

Referring now to FIG. 2D, a somewhat schematic block diagram of the ballast controller 200 implemented in accordance with the subject disclosure is shown. The ballast controller 200 includes one or more digital data processing devices and other electronics particularly suited to work in various embodiments of the subject disclosure. The ballast controller 200 preferably includes a printed circuit board with components for receiving, processing, displaying, and/or transmitting digital and/or analog data.

The ballast controller 200 includes a processor 250, which is generally logic circuitry that responds to and processes instructions. The processor 250 can include, without limitation, a central processing unit, an arithmetic logic unit, an application specific integrated circuit, a task engine, and/or any combinations, arrangements, or multiples thereof. The processor 250 is in communication with memory 252. Typical memory 252 includes random access memory (RAM), read only memory (ROM), mechanisms and structures for performing 1/0operations, and a storage medium such as a magnetic hard disk drive(s). The memory 252 includes software 254 and a plurality of modules as needed to perform the functions of the subject technology. Alternatively, one or more of the modules could be embodied as an all hardware device on one or more printed circuit boards or the like.

For example, the software 254 may include an operating system for execution on the processor 250. Software or code generally refers to computer instructions which, when executed on one or more digital data processing devices, cause interactions with operating parameters, sequence data/parameters, database entries, network connection parameters/data, variables, constants, software libraries, and/or any other elements needed for the proper execution of the instructions, within an execution environment in memory.

The memory 252 also has plurality of modules. A module is a functional aspect, which may include software and/or hardware. Typically, a module encompasses the necessary components to accomplish a task. It is envisioned that the same hardware (e.g., memory and processor) could implement a plurality of modules and portions of such hardware being available as needed to accomplish the task.

For example, a database module 256 creates, stores and maintains multiple databases necessary for the proper operation of the subject technology. A program module 258 stores an instruction set to allow the operator to program operation and otherwise interact with the ballast controller 200. An algorithm module 260 stores an instruction set to allow the processor to apply one or more algorithms to operation of the ballast controller 200 as well as vary the actual algorithms according to user input.

The ballast controller 200 also has input and output devices such as buttons 262 or a keypad and a display 210, respectively. The buttons 262 may have any number of buttons, dials, selector switches and the like as necessary to accomplish operation in accordance with the subject technology.

Still referring to FIG. 2D, the ballast controller 200 also includes a WiFi module 264 and/or wired communication channels to facilitate communication with external sensors, networks, devices, elements and the like. Those of ordinary skill will recognize that the hardware, software, modules, sensors, elements, devices and various processes discussed herein are merely exemplary of the structure and functionality performed by the disclosed technology and thus such hardware and processes (and/or their equivalents) may be implemented in commercial embodiments in various combinations without materially affecting the operation of the disclosed technology. It is also envisioned that the ballast controller 200 and/or other components may be incorporated into a more comprehensive site controller that controls the operation of additional systems (e.g., heating and air conditioning) along with additional sensors and the like.

Referring again to FIGS. 2A-2C, the housing 102, the ballast controller 200 and UV source 300 couple to a mounting bracket 150. In brief overview, the UV source 300 is keyed to the mounting bracket 150 so that an inappropriate UV source does not properly fit in the mounting bracket 150. Further, the ballast controller 200 also recognizes usage of a proper UV source 300 and prevents operation when an improper UV source is connected and when the UV source 300 is removed.

Figures 3A, 3B:
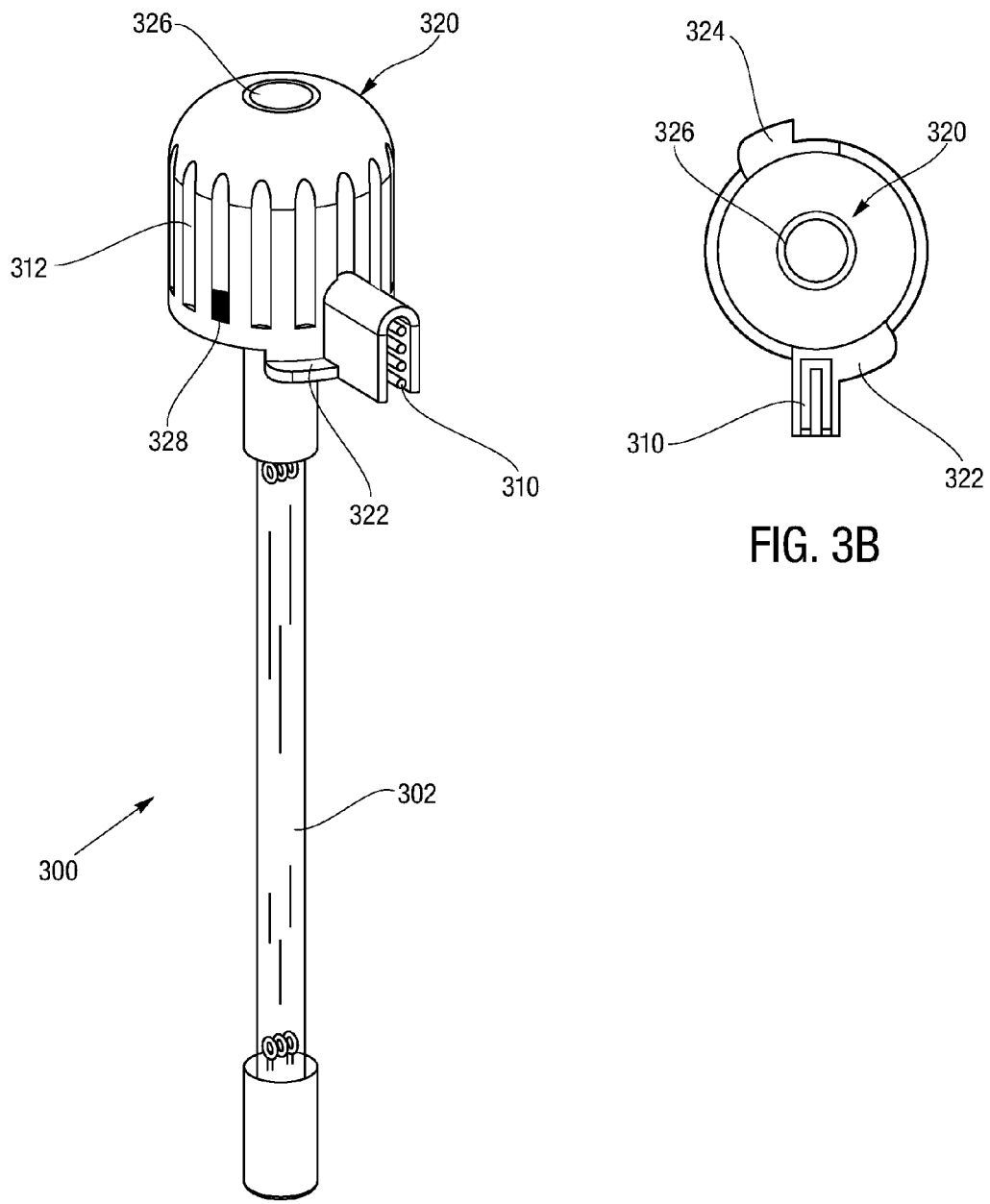
FIG. 3A is a perspective view of a UV source in accordance with the subject technology.
FIG. 3B is a top view of a UV source in accordance with the subject technology.

Referring now to FIG. 3A, a perspective view of a UV bulb assembly 300 for the UV source 300 in accordance with the subject technology is shown. The UV bulb assembly 300 includes a cap assembly 320 coupled to a bulb 302. When mounted in the UV assembly 100, the bulb 302 is protected by a sleeve 304 and centrally located in the interior chamber 106 of the housing 102 (see FIG. 2A). The quartz sleeve 304 allows for transmission of UV light while minimizing the temperature fluctuation effect and protecting the bulb 302 during use.

The cap assembly 320 is generally dome-shaped and includes a bulb connector 310 and knurled manual grip area 312. The cap assembly 320 also includes a rear locking tab 324 (best seen in FIG. 4A) and a front locking tab 322 adjacent the bulb connector 310. The opposing tabs 322, 324 are designed to provide a turn-to-lock engagement with the mounting bracket 150. The cap assembly 320 also includes an inner flange 326 for coupling the cap assembly 320 to the bulb 302.

An RFID tag 328 is mounted inside the cap assembly 320 for verifying proper lamp installation. The RFID tag 328 consists of a High Frequency (HF) antenna tuned to transmit and receive at 13.56 MHz (other frequencies may be utilized) and coupled to an integrated circuit (not shown) within the RFID tag 328. The integrated circuit (IC) is powered through energy received from a HF antenna when in the presence of an electromagnetic field. When not in the presence of an electromagnetic field, the IC remains passive and does not consume or radiate energy through the HF antenna. The IC contains a unique serial number and digital memory for storing custom user information including, but not limited to, lamp type, lamp serial number, lamp usage, lamp control parameters and the like. Information is written to and read from the IC through the HF antenna by modulating the electromagnetic field in proximity to the tag. As a result, information travels with the UV source 300 and can be read by the ballast controller 200.

Figure 4A:
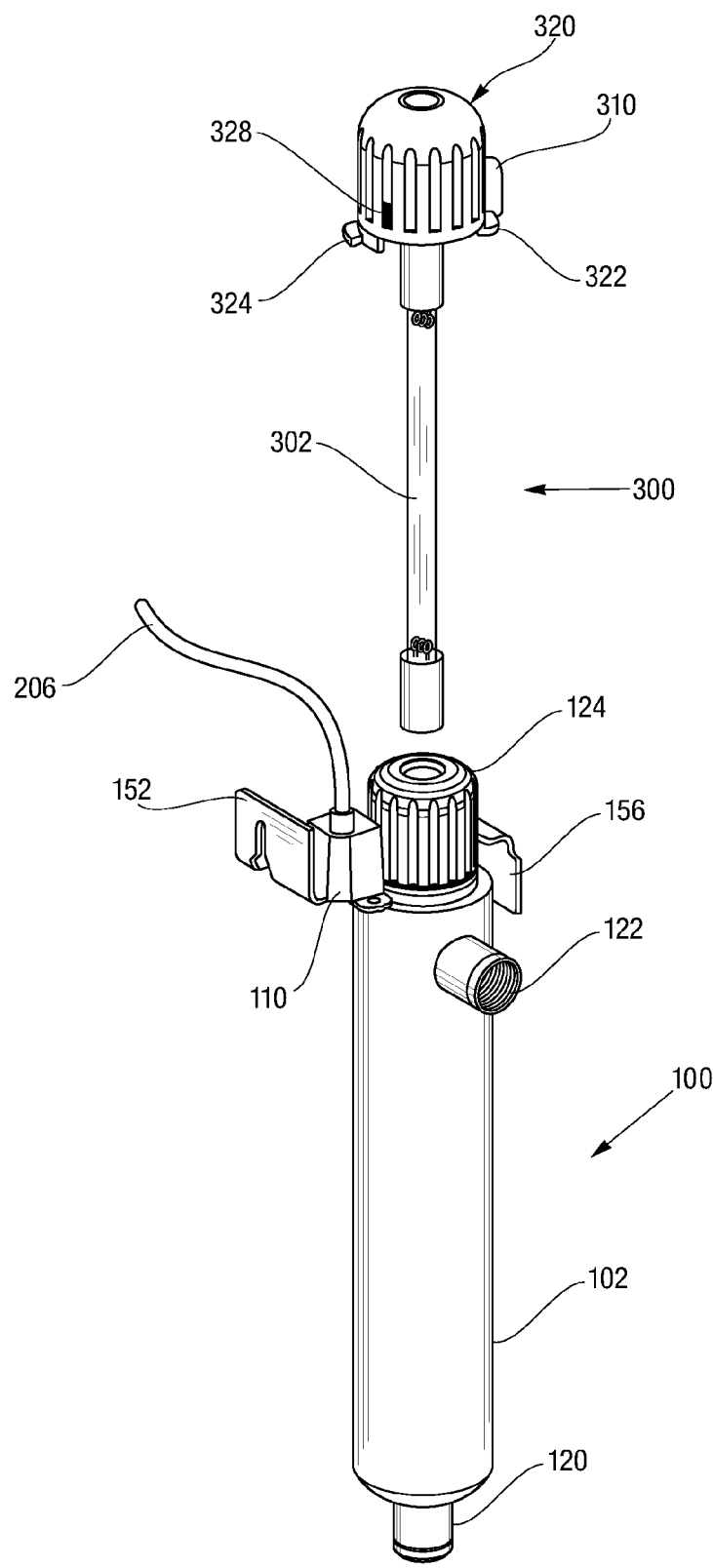
FIG. 4A is an exploded perspective view of a UV assembly in accordance with the subject technology.

Referring now to FIG. 4A, a perspective exploded view of the UV assembly 100 with the mounting bracket 150 partially cut-away is shown. The housing 102 defines an inlet 120 and an outlet 122 so that fluid flows through the interior chamber 106 for treatment. A top 124 of the housing 102 is configured to sealingly engage the UV source 300 so that the bulb 302 is centrally located within the housing 102 in a fluid tight manner. The top 124 preferably threads onto the housing 102 and contains an inner seal (not shown) for preventing fluid leakage from the housing 102. The housing 102 also couples to the mounting bracket 150. In one embodiment, the housing 102 is glued to the mounting bracket 150.

Figure 4B:
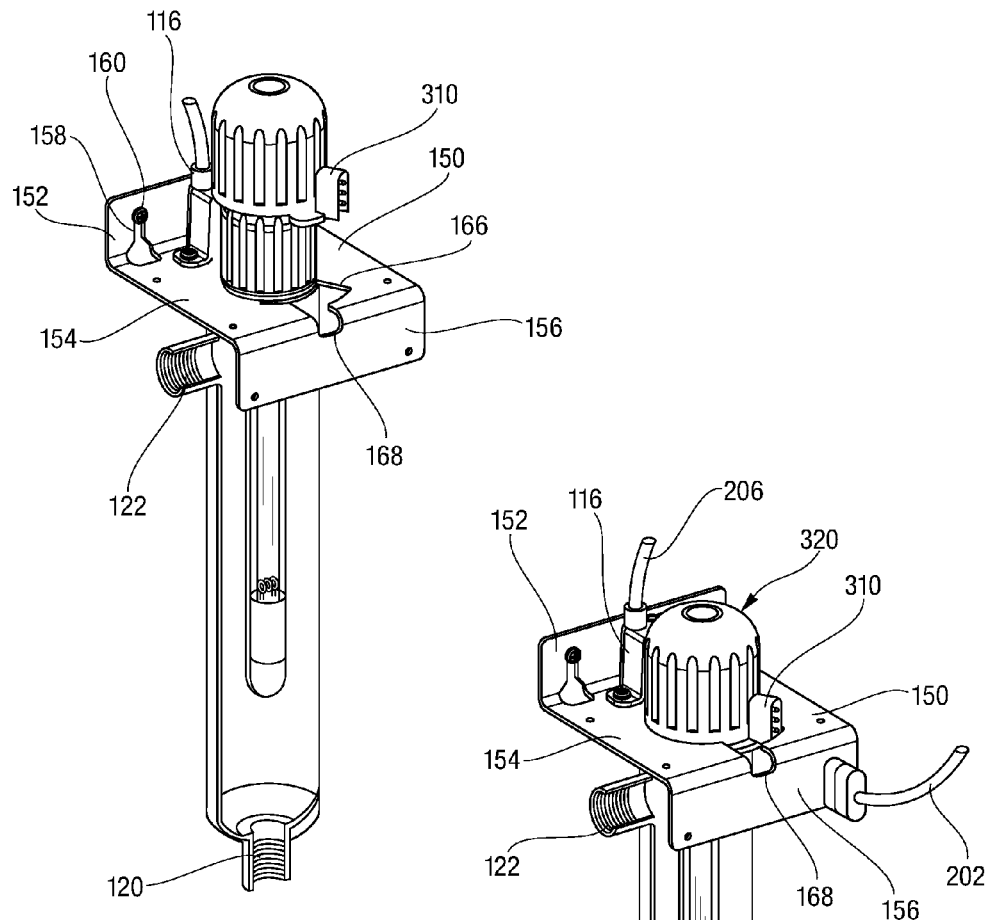
FIG. 4B is an exploded perspective view of a UV assembly being assembled in accordance with the subject technology.
Figure 4C:
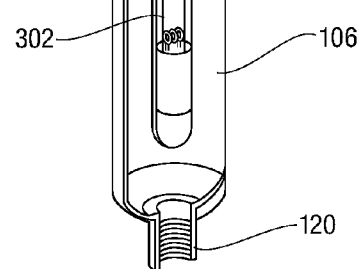
FIG. 4C is an exploded perspective view of a UV assembly almost fully assembled in accordance with the subject technology.

Referring additionally to FIGS. 4B and 4C, perspective views of the UV source 300 being secured in the housing 102 are shown. The mounting bracket 150 couples to an antenna housing 116 with an RFID antenna 110 therein. The RFID antenna 110 is configured to interact with the RFID tag 328 as described herein. The mounting bracket 150 is generally formed by bending a flat plate to create a rear portion 152 upstanding from a central portion 154 and a front portion 156 depending from the central portion 154. The upward rear portion 152 defines two keyholes 158 for easily mounting the bracket 150, and thereby the UV assembly 100, on fasteners 160.

The central portion 154 of the mounting bracket 150 defines a central opening 162 for retaining the housing 102. In one embodiment, the housing 102 is inserted into the central opening 162 without the top 124 so that screwing the top 124 to the housing 102 securely couples the mounting bracket 150 and housing 102 together. The central opening 162 also includes a rear slot 164 (best seen in FIG. 4A) and a front slot 166. The rear slot 164 is configured so that when the UV source 300 is positioned as shown in FIGS. 4B and 4C, the rear tab 324 passes there through. In other words, a shape of the rear slot 164 matches the rear tab 324 of the cap assembly 320.

Similarly, a shape of the front slot 166 matches the front tab 322 and bulb connector 310 so that, when positioned as shown in FIGS. 4B and 4C, the front tab 322 and bulb connector 310 pass there through. Once in position as shown in FIG. 4C, clockwise rotation of the UV source 300 captures the tabs 322, 324 under the mounting bracket 150 so that the UV source 300 is fixed longitudinally with the bulb 302 centered in the housing 102. Additionally, the bulb connector 310 aligns with a hollow portion 168 of the front portion 156. This hollow portion 168 allows coupling and decoupling the cable 202 to the bulb connector 310 only when the UV source 300 is properly positioned.

With the UV source 300 fully installed, it is not possible to remove the UV source 300 unless the cable 202 is disconnected because the tabs 322, 324 lock the UV source 300 in longitudinally and the cable 202 in the bulb connector 310 prevents rotation by virtue of orientation within the hollow portion 168 cut into the front portion 156 of the mounting bracket 150. Also, when the UV source 300 is in the fully installed position, the RFID tag 328 is aligned with the antenna housing 116, so as these two items are in close enough proximity to operate. Based upon a signal received from the antenna 110, the ballast controller 200 is able to control power to the UV source 300, determine if the UV source 300 is proper, determine a number of hours used for the particular UV source 300 and the like as described below.

To change the UV source 300, the cable 202 must be removed from the bulb connector 310. Then, the UV source 300 is rotated counterclockwise to release engagement of the tabs 322, 324 so that the UV source 300 can be pulled out of the housing 102 in an axial direction. Displacement of the UV source 300 from a fully installed position causes an increase in the distance between the antenna 110 and the RFID tag 328. Thus, requiring the cable 202 to be disconnected and reading the antenna signal act as duplicative safety measures to prevent inadvertent UV exposure when the UV source 300 is not properly positioned. For additional safety, as shown in FIG. 4D, if the cable 202 is inserted in the bulb connector 310 with the UV source 300 outside of the housing, the cable 202 prevents the UV source 300 from being coupled to the mounting bracket 150 for safety because the bulb connector 310 will not pass through the front slot 166. Additionally, the antenna signal, as read by the ballast controller 200, will prevent the UV source 300 from being powered on when the RFID tag 326 is not adjacent the antenna housing 116 even if the cable 202 is connected.

UV Assembly with Flow Switch

Another embodiment of the subject technology includes a flow switch for providing a signal to the ballast controller 200 to indicate whether or not fluid is flowing through the housing 102. As a result, the UV source 300 may be dimmed or even turned off to conserve energy when fluid is not flowing or flowing slowly. In still another embodiment, the UV assembly 100 is part of a fluid network that includes a flow sensor (not shown). The flow sensor may be part of the UV assembly 100. The flow sensor provides a flow rate to the ballast controller 200, which adjusts the output of the UV source 300 based upon the flow rate.

Figure 5A:
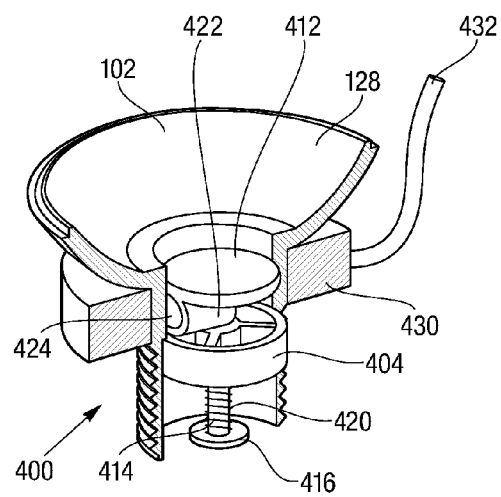
FIGS. 5A and 5B, are cross-sectional views of a flow switch in a closed position (e.g., no fluid flow) in accordance with the subject technology.
Figure 5B:
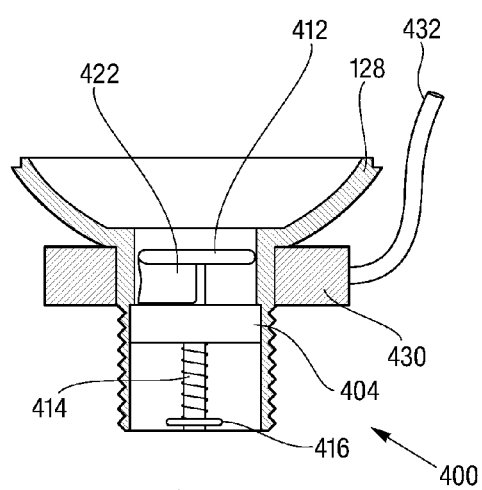
Figure 6A:
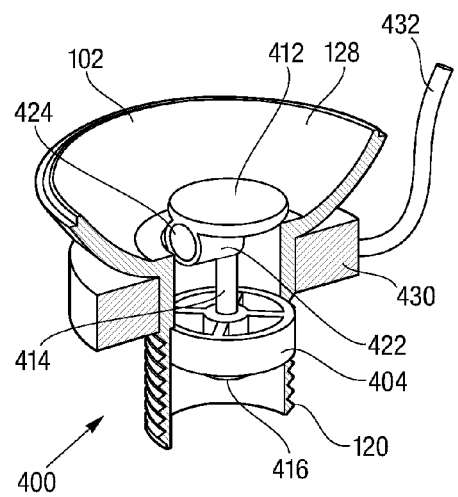
FIGS. 6A and 6B are cross-sectional views of a flow switch in the open position (e.g., fluid flow) in accordance with the subject technology.
Figure 6B:
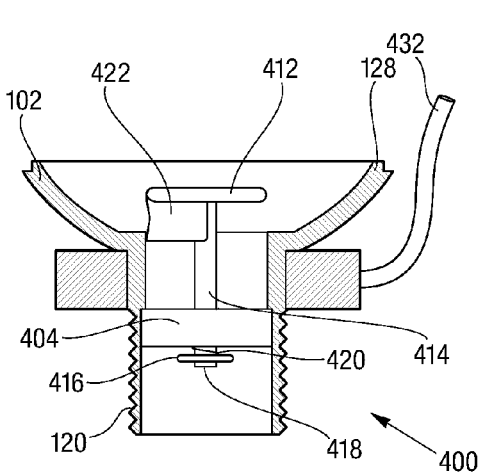

Referring now to FIGS. 5A and 5B, a flow switch 400 in accordance with the subject technology is shown in cross-sectional view in a closed position (e.g., no fluid flow). The housing 102 has an increasing diameter portion 128 adjacent the inlet 120. The flow switch 400 mounts in the increasing diameter portion 128 of the interior chamber 106 by, for example, coupling to the inlet 120. FIGS. 6A and 6B are cross-sectional views of the flow switch 400 in the open position (e.g., fluid flow).

Figure 7:
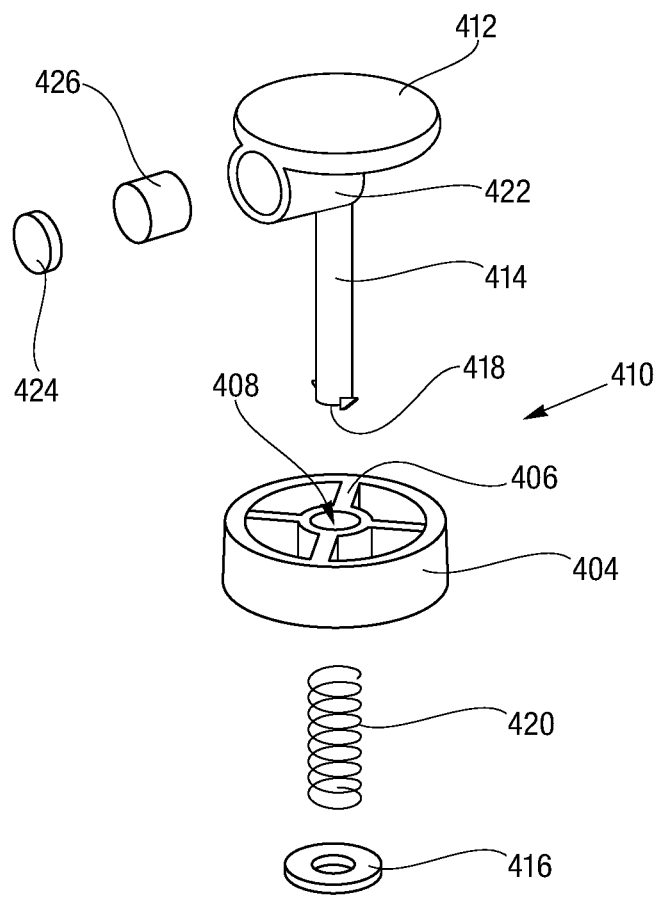
FIG. 7 is an exploded view of the flow switch in accordance with the subject technology.

Referring now to FIG. 7, an exploded view of the flow switch 400 is shown. The flow switch 400 includes a shaft guide 402 that is fixes in the inlet 120. The shaft guide 402 may be glued, welded, snap fit or otherwise secured in place. The shaft guide 402 has a ring shaped body 404 with internal vanes 406 defining a central aperture 408. Thus, the shaft guide 402 provides a plurality of flowpaths through the inlet 120.

A plunger assembly 410 is slidably mounted in the central aperture 408 for up and down motion depending upon the status of fluid flow. The plunger assembly 410 has a disc 412 mounted on a shaft 414. In particular, it is the shaft 414 captured in the central aperture 408. The disc 412 is sized and configured to move within the inlet 120. A collar 416 couples to a distal end 418 of the shaft 414 for retaining the shaft 414 within the central aperture 408. A spring 420 surround the shaft 414 adjacent the collar 416. By pushing against the guide 402, the spring 420 biases the disc 412 toward a closed position. The plunger assembly 410 also includes a cylinder 422 holding a magnet 424. A spacer 426 in the cylinder 422 positions the magnet 424 radially outward. When flow against the disc 412 moves the shaft 414 up, the magnet 424 moves with the shaft 414.

Referring again to FIGS. 5A, 5B, 6A and 6B, in order to sense the position of the magnet 424, and thereby whether or not fluid is flowing, a sensor 430 is mounted to the housing 102. The sensor 430 provides a signal to the ballast controller 200 via cable 432. In the closed position, during little or no flow through the inlet 120, the spring 420 biases the plunger assembly 400 so that the disc 412 is in the inlet 120 and the magnet 424 is aligned for detection by the sensor 430. In the open position during flow through the inlet 120, the flow applies pressure to move the disc 412 into the increased diameter portion 128 of the housing 102 and, in turn, the magnet 424 moves out of proximity so as not to be detected by the sensor 430. In short, starting and stopping flow causes the sensor 430 to change state. As could be appreciated by those of ordinary skill in the art, the flow switch 400 provides an indication of very low flow because minimal flow is required to push the disc 412 upward.

Operation

The subject technology provides features that facilitate safe operation and maintenance of the UV assembly 100. In operation, the ballast controller 200 has will first check for a valid RFID tag 328 being adjacent the antenna 110 before attempting to send power to UV source 300. If a valid RFID tag 328 is not detected, then the ballast controller 200 will not attempt to send power to the UV source 300. Therefore, if the UV source 300 is connected via cable 202 slightly outside of the interior chamber 106, the RFID tag 328 will not be detected due to distance from the antenna housing 116 and the UV source 300 will not produce UV light.

In order to install a new UV source 300, the tabs 322, 324 must pass through the respective slot 164, 166, which is prevented if the cable 202 is connected. Only once the UV source 300 has been inserted and rotated into a locked position with the connector 310 oriented in the hollow 168 can the cable 202 be connected. Thus, in addition to the ballast controller 200 requiring a proper signal from the RFID antenna 110 by virtue of proper installation, there is a mechanical structure to further insure proper installation. Additionally, the flow switch 400 provides a signal to the ballast controller 200 indicating whether or not fluid flow is present. As a result, when there is no fluid flow, the ballast controller 200 can dim or power down the lamp to conserve energy.

Further, the ballast controller 200 can record the operational statistics of the UV source such as run time, run time at full power, run time dimmed and the like to provide particular indication that replacement is needed. These parameters can also be stored in the RFID tag 328 so that removal and replacement of a UV source 300 cannot circumvent periodic replacement. The ballast controller 200 may provide reminders to replace the UV source 300 after a certain amount of usage in time or power output. The ballast controller 200 can even power down the UV source 300 after a predetermined threshold of usage is reached.

In order to subsequently remove the UV source 300 for replacement, it is necessary to disconnect the cable 202 from the connector 310 (which prevents the UV light from being produced). Then, the UV source 300 can be rotated counter-clockwise and lifted out of the housing 102. Further, the UV source 300 moving away from the housing 102 takes the RFID tag 328 away from the antenna 110 so that the signal generated thereby, as processed by the ballast controller 200, prevents power to the UV source 300 as well. This combination of RFID tag to prevent generation of UV light coupled with mechanical locking is safer and more reliable than using the RFID tag alone, as it prevents the possibility of ballast controller malfunctioning and timing issues. Once the UV source has been disconnected from the ballast controller via the cable, the ballast controller can be reset. For example, ballast controller power can be cycled or a manual reset button can be pressed in order to ready the ballast controller to attempt to restart a UV source.

As would be appreciated by those of ordinary skill in the art the subject technology is applicable to agriculture, aquaculture, breweries, bottling plants, cooling towers, dairies, the electronics industry, food, beverages, hospitals, laboratories, pharmaceuticals, potable drinking water, swimming pools, and the like.

While the invention has been described with respect to preferred embodiments, those skilled in the art will readily appreciate that various changes and/or modifications can be made to the invention without departing from the spirit or scope of the invention. For example, each claim may depend from any or all claims, even in a multiple dependent manner, even though such has not been originally claimed.

What is claimed is:

1. An ultra-violet (UV) light source assembly for treating a fluid with UV light comprising:
   a tubular housing defining: an interior chamber having a treatment zone; an inlet; and an outlet so that the fluid entering the inlet passes through the treatment zone;
   a mounting bracket coupled to the tubular housing, the mounting bracket defining at least one slot and a hollow;
   a UV source mounted in the interior chamber for supplying UV light to the treatment zone, the UV source includes: at least one tab that twist-locks in the slot; a connector that aligns with the hollow when locked for cabling to a ballast controller; and an RFID tag;
   an RFID antenna on the mounting bracket so that when locked, the RFID antenna interacts with the RFID tag to emit a first signal indicating position of the UV source; and
   a flow switch sending a second signal indicating fluid flow for the interior chamber, the flow switch includes: a guide fixed in the inlet; a shaft mounted to the guide for sliding motion; a disc on a first end of the shaft so that flow against the disc moves the shaft; a collar coupled to a second end of the shaft for retaining the shaft within the guide; a spring mounted between the collar and the guide to bias the shaft toward a closed position; a magnet coupled to the shaft for motion therewith; and a sensor mounted to the housing for generating the second signal based on proximity of the magnet thereto,
   wherein, during little or no flow through the inlet, the spring biases the shaft so that the magnet is positioned to be detected by the sensor, and during flow through the inlet, the flow applies pressure to move the disc and, in turn, the magnet moves to be positioned to not be detected by the sensor.

2. An ultra-violet (UV) light source assembly as recited in claim 1, further comprising a ballast controller for receiving and processing the first and second signals, wherein the ballast controller powers the UV source based upon the first and second signals.

3. An ultra-violet (UV) light source assembly as recited in claim 2, wherein the ballast controller receives a signal indicating a flow rate and adjusts an output of the UV source based upon the flow rate.

4. An ultra-violet (UV) light source assembly as recited in claim 2, wherein the ballast controller records at least one operational statistic of the UV source to determine when to replace the UV source.

5. An ultra-violet (UV) light source assembly as recited in claim 4, wherein the at least one operational statistic is stored in the RFID tag.

6. An ultra-violet (UV) light source assembly as recited in claim 1, wherein the interior chamber is defined by a housing defining an inlet along an axis and a large diameter portion of the housing adjacent the inlet flares outward from the axis, the guide has a ring shaped body with internal vanes defining a central aperture for receiving the shaft.

7. An ultra-violet (UV) light source assembly for treating a fluid with UV light comprising:

a tubular housing defining: an interior chamber having a treatment zone; an inlet; and an outlet so that the fluid entering the inlet passes through the treatment zone;

a mounting bracket coupled to the tubular housing, the mounting bracket defining at least one slot and a hollow;

a UV source mounted in the interior chamber for supplying UV light to the treatment zone, the UV source includes: at least one tab that twist-locks in the slot; a connector that aligns with the hollow when locked for cabling to a ballast controller; and an RFID tag; and an RFID antenna coupled to the mounting bracket so that in when locked, the RFID antenna interacts with the RFID tag to emit a signal.

8. An ultra-violet (UV) light source assembly as recited in claim 7, wherein the at least one slot is two opposing slots and the at least one tab is two opposing tabs, the connector is adjacent one of the tabs, and at least one of the slots is sized to allow the tab and adjacent connector to pass therethrough.

9. A flow switch for an interior chamber, wherein the interior chamber is defined by a housing defining an inlet along an axis and a large diameter portion of the housing adjacent the inlet flares outward from the axis, the flow switch comprising:

a guide fixed in the inlet, the guide having a ring shaped body with internal vanes defining a central aperture surrounded by at leat one flowpath;

a plunger assembly having a disc and a shaft extending from the disc, wherein the shaft is coupled in the central aperture for sliding motion along the axis;

a collar coupled to a distal end of the shaft for retaining the shaft within the central aperture;

a spring mounted between the collar and the guide to bias the plunger assembly toward a closed position;

a magnet coupled to the plunger assembly for motion therewith; and a sensor mounted to the housing for determining proximity of the magnet, wherein, in the closed position during little or no flow through the inlet, the spring biases the plunger assembly so that the magnet is positioned to be detected by the sensor, and in an open position during flow through the inlet, the flow applies pressure to move the disc into the large diameter portion of the housing and, in turn, the magnet moves to be positioned to not be detected by the sensor.

* * * * *